US00PP30404P3

(12) United States Plant Patent
Koot

(10) Patent No.: US PP30,404 P3
(45) Date of Patent: Apr. 16, 2019

(54) ***CALIBRACHOA* PLANT NAMED 'DUEALNAGOGI'**

(50) Latin Name: ***Calibrachoa* sp.**
Varietal Denomination: Duealnagogi

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 49 days.

(21) Appl. No.: 15/530,755

(22) Filed: Feb. 22, 2017

(65) Prior Publication Data

US 2018/0242502 P1 Aug. 23, 2018

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC . A01H 5/02; A01H 5/00; A01H 5/025; A01H 6/821
See application file for complete search history.

(56) References Cited

U.S. PATENT DOCUMENTS

PP14,464 P2 * 1/2004 Pierce ..... A01H 5/02 Plt./413

OTHER PUBLICATIONS

Greenhouse Management Supplement 2016. New annual Varieties, retrieved on Jun. 11, 2018, retrieved from the Internet at http://giecdn.blob.core.windows.net/fileuploads/file/july_newvarieties.pdf, cover page, pp. 8-9,40. (Year: 2016).*
Mast Young Plants 2016-2017 Program The Plant Connection A Division of BFG Suppy Co. retrieved on Jun. 11, 2018, retrieved from the Internet at https://www.bfgsupply.com/_CE/pagecontent/Documents/Plant%20Connection/Mast.pdf, 5 pp. (Year: 2016).*

* cited by examiner

*Primary Examiner* — June Hwu
(74) *Attorney, Agent, or Firm* — C. A. Whealy

(57) ABSTRACT

A new and distinct cultivar of *Calibrachoa* plant named 'Duealnagogi', characterized by its compact, semi-upright to outwardly spreading, trailing and decumbent plant habit; freely branching habit; early and freely flowering habit; flowers with bright yellow-colored petals; and good garden performance.

1 Drawing Sheet

Botanical designation: *Calibrachoa* sp.
Cultivar denomination: 'DUEALNAGOGI'.

BACKGROUND OF THE INVENTION

The present invention relates to a new and distinct cultivar of *Calibrachoa* plant, botanically known as *Calibrachoa* sp. and hereinafter referred to by the name 'Duealnagogi'.

The new *Calibrachoa* plant is a product of a planned breeding program conducted by the Inventor in Rheinberg, Germany. The objective of the breeding program is to create new compact and early-flowering *Calibrachoa* plants with unique and attractive flowers.

The new *Calibrachoa* plant originated from a cross-pollination made by the Inventor in July, 2014 in Rheinberg, Germany of a proprietary selection of *Calibrachoa* sp. identified as code number AA13-002561-003, not patented, as the female, or seed, parent with a proprietary selection of *Calibrachoa* sp. identified as code number AA13-007042-001, not patented, as the male, or pollen, parent. The new *Calibrachoa* plant was discovered and selected by the Inventor as a single flowering plant from within the progeny of the stated cross-pollination in a controlled greenhouse environment in Rheinberg, Germany in May, 2016.

Asexual reproduction of the new *Calibrachoa* plant by vegetative terminal cuttings in a controlled greenhouse environment in Rheinberg, Germany since June, 2016 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duealnagogi'. These characteristics in combination distinguish 'Duealnagogi' as a new and distinct *Calibrachoa* plant:

1. Compact, semi-upright to outwardly spreading, trailing and decumbent plant habit.
2. Freely branching habit.
3. Early and freely flowering habit.
4. Flowers with bright yellow-colored petals.
5. Good garden performance.

The new *Calibrachoa* can be compared to plants of the female parent selection. Plants of the new *Calibrachoa* differ primarily from plants of the female parent selection in plant habit as plants of the new *Calibrachoa* are more compact than plants of the female parent selection. In addition, plants of the new *Calibrachoa* have larger flowers than plants of the female parent selection.

The new *Calibrachoa* can be compared to plants of the male parent selection. Plants of the new *Calibrachoa* differ primarily from plants of the male parent selection in flowering habit as plants of the new *Calibrachoa* flower earlier than plants of the male parent selection. In addition, plants of the new *Calibrachoa* and the male parent selection differ in flower color as plants of the male parent selection have reddish yellow-colored flowers.

Plants of the new *Calibrachoa* can be compared to plants of *Calibrachoa* sp. 'Cal Yel', disclosed in U.S. Plant Pat. No. 14,464. In side-by-side comparisons, plants of the new *Calibrachoa* differ primarily from plants of 'Cal Yel' in the following characteristics:

1. Plants of the new *Calibrachoa* are more compact than plants of 'Cal Yel'.
2. Plants of the new *Calibrachoa* are more freely flowering than plants of 'Cal Yel'.

BRIEF DESCRIPTION OF THE PHOTOGRAPH

The accompanying colored photograph illustrates the overall appearance of the new *Calibrachoa* plant showing the colors as true as it is reasonably possible to obtain in colored reproductions of this type. Colors in the photograph may differ slightly from the color values cited in the detailed botanical description which accurately describe the colors of the new *Calibrachoa* plant.

The photograph is a side perspective view of a typical flowering plant of 'Duealnagogi' grown in a container.

DETAILED BOTANICAL DESCRIPTION

The aforementioned photograph and following observations, measurements and values describe plants grown during the summer in 22-cm containers in a glass-covered greenhouse in Rheinberg, Germany and under cultural practices typical of commercial *Calibrachoa* production. During the production of the plants, day and night temperatures averaged 18° C. and light levels averaged 4,500 lux. Rooted young plants were pinched one time three weeks after planting and were 16 weeks old when the photograph and description were taken. In the following description, color references are made to The Royal Horticultural Society Colour Chart, 2001 Edition, except where general terms of ordinary dictionary significance are used.

Botanical classification: *Calibrachoa* sp. 'Duealnagogi'.

Parentage:

*Female, or seed, parent.*—Proprietary selection of *Calibrachoa* sp. identified as code number AA13-002561-003, not patented.

*Male, or pollen, parent.*—Proprietary selection of *Calibrachoa* sp. identified as code number AA13-007042-001, not patented.

Propagation:

*Type.*—By vegetative cuttings.

*Time to initiate roots, summer.*—About five days at temperatures about 20° C.

*Time to initiate roots, winter.*—About seven days at temperatures about 20° C.

*Time to produce a rooted young plant, summer.*—About three weeks at temperatures about 20° C.

*Time to produce a rooted young plant, winter.*—About four weeks at temperatures about 20° C.

*Root description.*—Fine, fibrous; typically white in color, actual color of the roots is dependent on substrate composition, water quality, fertilizers, substrate temperature and age of roots.

*Rooting habit.*—Freely branching; medium density.

Plant description:

*Plant and growth habit.*—Compact, semi-upright to outwardly spreading to trailing and decumbent plant habit; freely branching habit with about seven primary lateral branches developing per plant; pinching enhances branching; dense and full appearance; vigorous growth habit; moderate growth rate.

*Plant height.*—About 24 cm.

*Plant diameter.*—About 68 cm.

Lateral branch description:

*Length.*—About 48 cm.

*Diameter.*—About 4 mm.

*Internode length.*—About 1.5 cm.

*Strength.*—Strong.

*Aspect.*—Initially upright to outwardly spreading to trailing and decumbent.

*Texture.*—Pubescent.

*Color.*—Close to 144B.

Leaf description:

*Arrangement.*—Before flowering, alternate, and after flowering, opposite; simple.

*Length.*—About 3 cm.

*Width.*—About 1 cm.

*Shape.*—Oblanceolate.

*Apex.*—Rounded.

*Base.*—Cuneate.

*Margin.*—Entire.

*Texture and luster, upper and lower surfaces.*—Pubescent; matte.

*Venation pattern.*—Pinnate; arcuate.

*Color.*—Developing leaves, upper and lower surfaces: Close to 144A. Fully expanded leaves, upper surface: Close to 144A; venation, close to 144A. Fully expanded leaves, lower surface: Close to 146B; venation, close to 146B.

*Petioles.*—Length: About 3.2 mm. Diameter: About 1.6 mm. Texture, upper and lower surfaces: Pubescent. Color, upper surface: Close to 144B. Color, lower surface: Close to 145A.

Flower description:

*Flower arrangement and habit.*—Single salverform flowers arising from leaf axils; freely flowering habit with usually about 420 to 460 flowers developing per plant during the flowering season; flowers face upright to outwardly.

*Fragrance.*—None detected.

*Natural flowering season.*—Early flowering habit, plants of the new *Calibrachoa* initiate and develop flowers about four to five weeks after planting; plants flower continuously from the spring throughout the summer in Germany.

*Flower longevity.*—Individual flowers last about seven to ten days on the plant; flowers not persistent.

*Flower diameter.*—About 2.4 cm.

*Flower length (height).*—About 2.1 cm.

*Flower throat diameter.*—About 5.6 mm.

*Flower tube length.*—About 1.3 cm.

*Flower tube diameter, base.*—About 1.8 mm.

*Flower buds.*—Length: About 1.7 cm. Diameter: About 3.8 mm. Shape: Elongated oblong. Texture: Pubescent. Color: Close to 5A and 154C.

*Corolla.*—Arrangement: Five petals fused at the base and opening into a flared trumpet; moderate to strongly lobed. Petal length from throat: About 1.4 cm. Petal lobe width: About 1.3 cm. Petal shape: Roughly spatulate. Petal apex: Rounded. Petal margin: Entire. Petal texture and luster, upper and lower surfaces: Smooth, glabrous; matte. Throat texture: Smooth, glabrous. Tube texture: Smooth, glabrous. Color: Petal, when opening, upper surface: Close to 5A. Petal, when opening, lower surface: Close to 5C. Petal, fully opened, upper surface: Close to 9B; venation, close to 11A, color does not change with development. Petal, fully opened, lower surface: Close to 4C; venation, close to 2B. Throat: Close to 9B; venation, close to 11A. Tube: Close to 4C; venation, close to 200A.

*Calyx.*—Arrangement: Star-shaped calyx with five sepals; sepals fused at the base. Sepal length: About 1.5 cm. Sepal width: About 2.1 mm. Sepal shape: Lanceolate. Sepal apex: Acute. Sepal margin: Entire. Sepal texture and luster, upper and lower surfaces: Pubescent; matte. Color, upper and lower surfaces: Close to 137A.

*Peduncles.*—Length: About 1.4 cm. Diameter: About 1 mm. Angle: About 45° from stem axis. Strength: Moderately strong. Texture: Pubescent. Color: Close to 144B.

*Reproductive organs.*—Stamens: Quantity: Six per flower. Filament length: About 8.8 mm. Filament color: Close to 150C. Anther shape: Ellipsoidal. Anther length: About 0.8 mm. Anther color: Close to 11A. Pollen amount: Scarce. Pollen color: Close to 8A. Pistils: Quantity: One per flower. Pistil length: About 8.8 mm. Style length: About 7.8 mm. Style color: Close to 145A. Stigma shape: Ellipsoidal. Stigma color: Close to 144A. Ovary color: Close to 144C. Seeds and fruits: Seed and fruit development have not been observed on plants of the new *Calibrachoa.*

Garden performance: Plants of the new *Calibrachoa* have been observed to have good garden performance and tolerate wind, rain and temperatures ranging from about 5° C. to about 40° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'Duealnagogi' as illustrated and described.

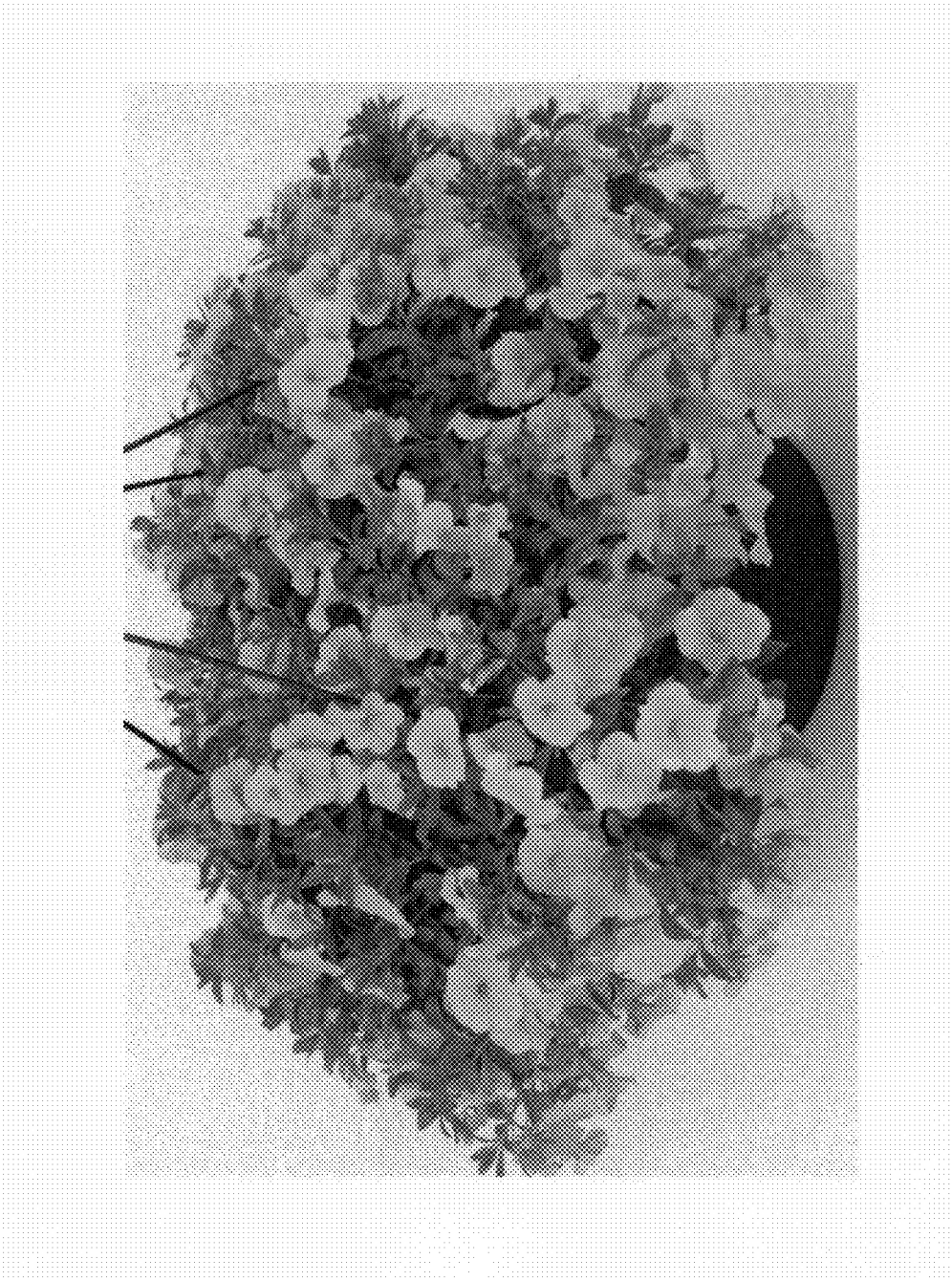

* * * * *